United States Patent [19]

Prangley

[11] Patent Number: 5,086,770
[45] Date of Patent: Feb. 11, 1992

[54] THERAPEUTIC APPARATUS WITH JEWELS

[76] Inventor: Gordon N. Prangley, 4 Church Street, Abbey Green, Bath, Avon, United Kingdom

[21] Appl. No.: 657,373

[22] Filed: Feb. 19, 1991

Related U.S. Application Data

[63] Continuation of Ser. No. 935,075, Nov. 24, 1986, abandoned, which is a continuation of Ser. No. 530,590, Jul. 11, 1983; abandoned.

[30] Foreign Application Priority Data

Nov. 11, 1981 [GB] United Kingdom ............... 8134029

[51] Int. Cl.⁵ ............................................ A61B 17/36
[52] U.S. Cl. ............................ 128/395; 606/13
[58] Field of Search .................... 128/20-23, 128/395-398, 379, 804; 600/26, 27; 606/2, 13, 17, 18, 27; 362/35

[56] References Cited

U.S. PATENT DOCUMENTS

| | | | |
|---|---|---|---|
| 1,510,080 | 9/1924 | Murphy | 128/395 |
| 1,684,081 | 9/1928 | Akers | 128/395 |
| 1,904,901 | 4/1933 | Lawrence | 362/35 |
| 3,618,193 | 11/1971 | Anderson et al. | 428/632 |
| 4,286,193 | 8/1987 | King et al. | 315/175 |

FOREIGN PATENT DOCUMENTS 2823615 12/1979 Fed. Rep. of Germany ...... 128/396

*Primary Examiner*—Max Hindenburg
*Attorney, Agent, or Firm*—Cushman, Darby & Cushman

[57] ABSTRACT

Apparatus for producing a therapeutic radiation beam has a light/heat source (45) disposed behind a shield (42). The shield (42) is an apertured disc of silver or gilded copper. It has a multiplicity of apertures (43) in which there are jewels (48). There may be a gold reflector (46) behind the light/heat source (45). The shield (42) may be rotatable at 1350 r.p.m. The source (45) may be electric bulb(s), selectively feedable with AC or DC power. The shield (42) is heated thereby, and radiation emerging forwardly of the shield has been altered by its passage through the jewels (48) etc. to attain therapeutic properties.

10 Claims, 3 Drawing Sheets

THERAPEUTIC APPARATUS WITH JEWELS

This is a continuation of application Ser. No. 06/935,075, filed on Nov. 24, 1986, now abandoned, which is a continuation of application Ser. No. 530,590, filed July 11, 1983, which is abandoned.

BACKGROUND OF THE INVENTION

The present invention relates to therapeutic apparatus for producing therapeutic radiation.

SUMMARY OF THE INVENTION

According to the present invention there is provided therapeutic apparatus comprising:

a shield comprising a plate penetrated by a multiplicity of apertures, and a multiplicity of jewels located in respective said apertures; and a source of thermal and/or optical radiation located rearwardly of the shield, so that radiation from the source is transmissible through the shield via at least some of the jewels.

Preferably said jewels are of a plurality of types differing in radiation absorption characteristics.

The radiation which emerges forwardly of the shield has been affected by its passage from the source. Indeed, under some circumstances it may be more correct to regard it as a different form of radiation from that produced by the source. This new or altered radiation may for convenience be referred to as "GP rays".

The plate is generally metallic, and may be of silver. Alternatively it may be of copper and, preferably, gold plated. The disc may be paraboloidal, convex rearwardly. Or it may be planar, as is more convenient for large units. In some embodiments it is rotatable, though it may instead be fixed, according to the treatment required.

Preferably a reflector is located rearwardly of the radiation source. This is preferably of gold, at least at the reflecting surface. (E.g. it may be of gold-plated copper.) It may be paraboloidal, similarly to the plate.

The radiation source may be a multiplicity of lightbulbs disposed generally symmetrically in an annular array. Alternatively, there may be one or more centrally placed bulbs, preferably of quartz-halogen type since these show little dimming with age. In either case, the bulb(s) can provide both heat and light. They are preferably located sufficiently close to the shield and reflector (if present) for these to be substantially heated by them.

The shield will generally have an axially symmetric array of apertures, with a symmetric distribution of sizes and types of jewels.

There may be a conducting coil mounted on the rear of the reflector (but electrically insulated from it), and means for supplying it with an alternating electrical signal In a preferred embodiment the shield is rotatable at 1000-1500 rpm, most preferably at 1350 rpm. It is believed that magnetic and other fields may act on the jewels to affect the production of GP rays. Therefore the rotation is preferably effected by a well shielded motor.

BRIEF DESCRIPTION OF THE DRAWINGS

Some embodiments of the invention will now be described in greater detail with reference to the accompanying drawings, in which.

DESCRIPTION OF THE PREFERRED EMBODIMENTS

Figure 1:
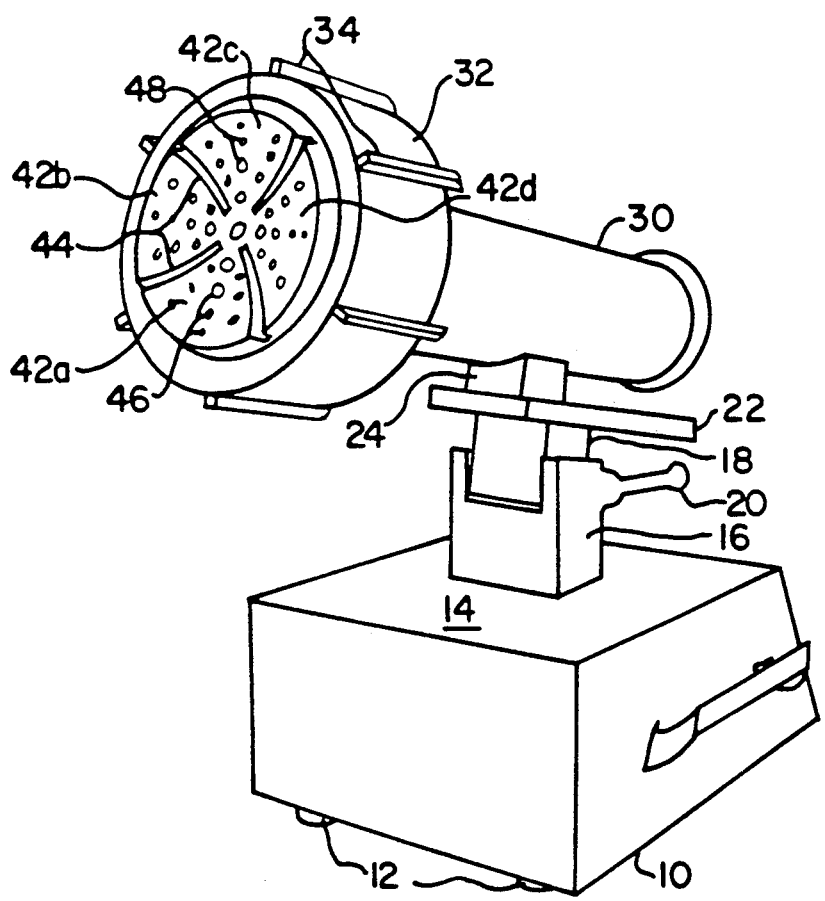
FIG. 1 is a perspective view of a first embodiment of apparatus according to the invention.

As may be seen from FIG. 1, the first embodiment of the apparatus has a base cabinet 10 mounted on four feet 12. The cabinet 10 has a generally horizontal upper surface 14, from the middle of which a mounting block 16 extends upwardly. This mounting block 16 has a generally U-shaped upper section, between the arms of which a platform member 18 is pivoted. The mounting block 16 has a mechanism, operable by means of a handle 20, by means of which the platform member 18 can be selectively allowed to pivot and locked in a desired position.

The platform member 18 includes a table element 22 on which is mounted a support block 24. The block 24 has a curved upper surface which is adapted to bear against the cylindrical surface of a tubular body 30. The body 30 extends forwardly and rearwardly of the block 24. At its rear end, it is closed by a wall comprising a grille. At the front, the body 30 is connected to or integral with a head 32 of greater diameter. The head 32 is generally cylindrical and coaxial with the body 30. It has a cylindrical wall portion 30' continuous with the body 30 Adjacent the front, the wall portion 30' has apertures 31. Radially outwardly spaced therefrom there is an outer shell 33 which has a plurality of longitudinal vanes 34 extending radially outwardly of its cylindrical surface. The annular space 37 between the wall portion 30' and the shell 33 is closed by front and rear portions 33 a,b. The rear portion 33 b is penetrated by apertures 35.

The base cabinet 10, tubular body 30, shell 33 and ancilliary components are fabricated from aluminium. The exterior of the shell is finished in mat black.

Figure 2:
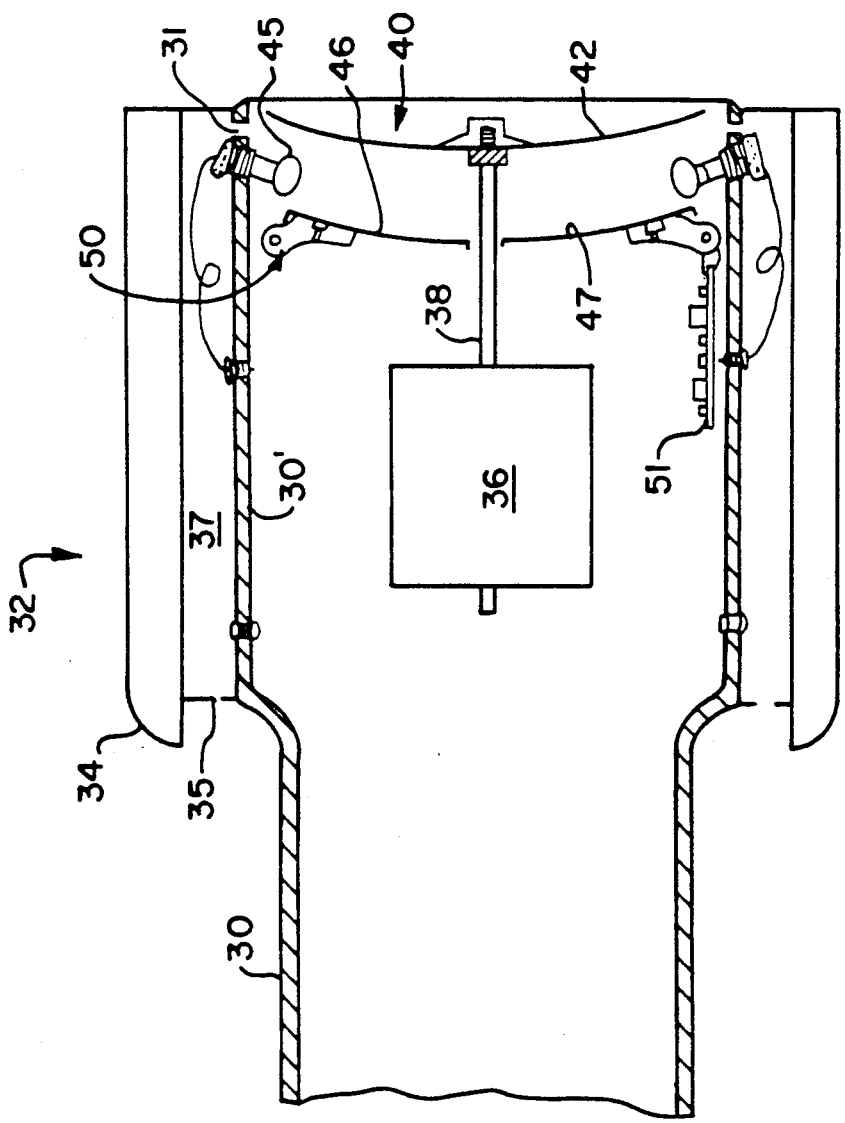
FIG. 2 is a longitudinal section through the head of the apparatus.

Referring now primarily to FIG. 2, it can be seen that mounted coaxially within the head 32, there is an electric motor 36, whose rotary shaft 38 extends forwardly to near the front of the head 32.

The motor is of a magnetically shielded type, since stray magnetic fields might impair the action of the apparatus.

A rotor 40 is mounted coaxially on the front portion of the shaft 38 for rotation therewith. The rotor 40 is also visible in FIG. 1, and it can be seen that it substantially closes the front head 32. The rotor 40 comprises a disc 42 of solid silver. The rotor 40 is substantially paraboloidal in shape, being coaxial with the shaft 38 and head 32. However, it preferably has a plurality (here four) of radial slots 44 (visible in FIG. 1), the disc portions 42a-d being to a small extent shaped or bent so that the rotor 40 can function as a fan.

The rotor 40 is penetrated by a symmetrical array of differently sized holes 43, each of which serves as a mounting for a precious or semi-previous stone. Stones 48 of several different types are used, the different types and sizes of stones being arranged to give an equal balance around the rotor 40. Preferably, each disc portion 42a-d contains a similar array of stones 48. Suitably, the stones are selected from: emerald, topaz, garnet, sapphire, ruby, diamond, peridot, and amethyst.

The emeralds may be synthetic ("grown"), whereas the rubies, sapphires etc may be chips of natural stones.

Axially behind the disc 42 (within the head 32) there is a circumferential array of electric lights 45. Preferably there are fifteen such lamps, each being rated 5 watts at 12 V, the lamps being symmetrically disposed around the head 32. A paraboloidal reflector 46 is mounted axially behind the lights 45. The reflector 46 is similar in size and shape to the disc 42, but has a central orifice through which the shaft 38 passes. The reflector 46 does not rotate, but is held stationary. Its reflecting (front) surface 47 is of gold. The reflector 46 may indeed be of solid gold, or of gilded copper.

The rotor 40 and the reflector 46 are quite closely spaced, being about ¾ to 1" (19 to 25 mm) apart in the illustrated embodiment.

In the illustrated embodiment, a copper coil 50 is concentrically mounted on the rear surface of the reflector 46, so as to be electrically isolated therefrom. The coil consists of a single turn of copper wire (⅛" gauge, i.e. 3 mm) with an overlap of ¾" (19 mm). The coil is adjacent the periphery of the reflector 46. A 1 KHz square wave generator 51 (0.5 W output) is connected to the coil 50.

At the rear end of the tubular body 30 there is a fan (not shown) for cooling the tube to maintain the rotor 40 etc in a desired temperature range. It draws air through the grille at the rear of the body 30, and passes it forwards into the head 32 where it passes through the apertures 31 in the front of the wall portion 30', rearwardly through the annular space 37, and out through the apertures 35.

The base cabinet 10 contains power supply leads and control gear, which will now be described with reference to FIG. 3. The upright rear face 60 of the cabinet 10 is a control panel, with a plurality of switches and indicators. Thus there are rotary controls 62 and 64 which operate respective triacs to control the electric power supplied to the lights 45 and the motor 36. The lights can thus be dimmed if desired. There are on-off switches and indicator lights associated with the power supplies for the motor 36, lights 45, cooling fan motor, and the square wave generator. An input socket 66 is provided for connecting a supply line of mains voltage electricity.

The main components located within the cabinet 10 are indicated schematically. There are in parallel a pair of transformers 70, each producing a 12 V output from the 240 V AC mains. Rectifying means are switchable by means of a relay 72. When rectification is affected, the rectified outputs from the transformers 70 are smoothed by means of large smoothing capacitors 74, suitably of 33,000 microfarad capacity. Thus, when operating in DC mode, a very smooth 12 V output can be obtained This output obtained via the transformers 70, whether rectified or not, is used to feed the lights 45, as will be described later. The cabinet 10 also contains a 12 V low current regulator for providing a power supply to the square wave generator. When this is on, an indicator lamp is lit.

For use, the apparatus may be placed on a table. A patient to be treated sits or stands before the head 32, and the apparatus is pivoted by means of the handle 20 so that the head points at the part of the patient's body which requires treatment. The apparatus is connected to the mains via the input 66. The motor 36 is operable at the full mains voltage, but it is supplied via the triac 64 so that its speed may be controlled. This is adjusted until a speed of 1,350 r.p.m. is attained. (For some purposes, speeds of up to 1,500 r.p.m. may be required.) The power to the lights 45 is increased by means of the triac 62. As the power to the lights 45 is increased, they become brighter and more heat is produced. The rotor 40 and reflector 46 will rapidly heat up, particularly as they are made of highly conductive metals. Radiation, optical and thermal, streams through the jewels 48 in the rotor, and may emerge as GP rays. The paraboloidal forms of the rotor and reflector cause a concentrated beam of the rays to be emitted.

Whether the lights 44 are fed with AC or DC power (selectable by means of the relay 72) depends on the nature of the ailment being treated. It has been found that migraine responds best when the lights are fed with DC, whereas rheumatic conditions respond best to AC treatment. In some cases, it may be advantageous to activate the 1 KHz square wave generator to feed its signal to the copper coil 50.

Figure 3:
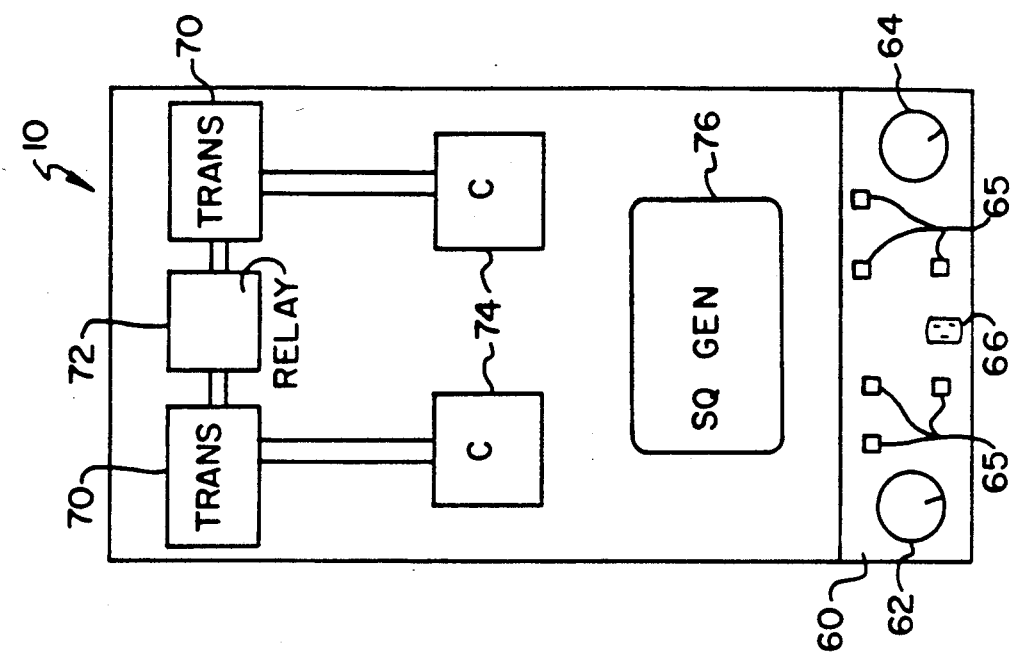
FIG. 3 is a schematic view of the control apparatus.

In apparatus shown in FIGS. 1 to 3 the rotor is intended to revolve at a rate in the range 1,350 to 1,500 r.p.m. However, it is possible to obtain therapeutic effects at other speeds, or even without any rotation whatsoever. In such cases it may be necessary to employ larger gemstones 48 than are necessary when the preferred rate of rotation is employed.

Figure 4:
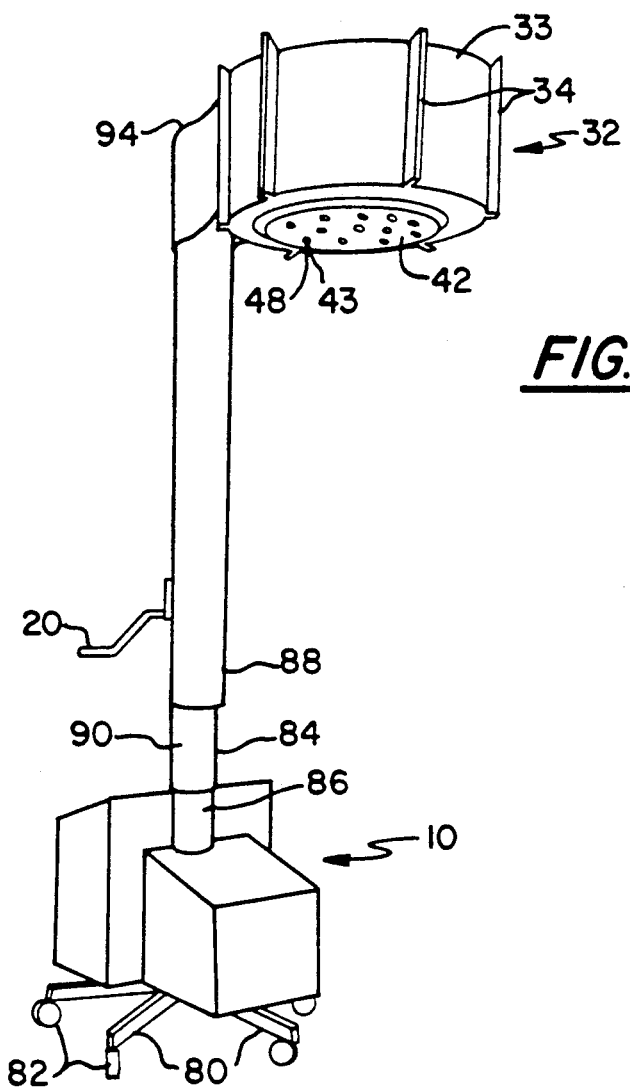
FIG. 4 is a perspective view of a second embodiment.
Figure 5:
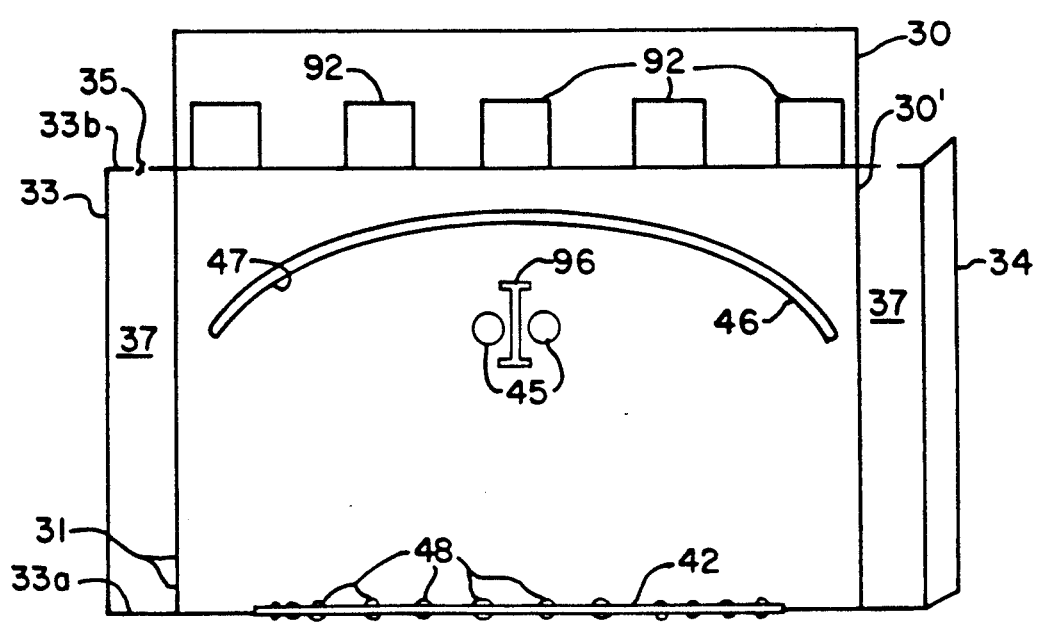
FIG. 5 is a schematic longitudinal section on a larger scale through the head of the second embodiment.

FIGS. 4 and 5 show a non-rotary embodiment. It has some other differences from the first embodiment: it is larger and has its axis upright; and the disc 42 is planar. But in most respects it is similar, and the same reference numerals are used for corresponding elements.

The base cabinet 10 is mounted on a stand 80 provided with wheels 82. The cabinet 10 houses equipment and controls much as for the first embodiment, *mutatis mutandis* (in the absence of a motor 36 and coil 50). A tubular column 84 extends upwardly from a mounting 86 in the cabinet 10. A head support tube 88 fits slidably over it. The column 84 has a rack surface 90 which is engaged by a pinion associated with the tube 88. The pinion is rotatable by means of a handle 20 or handwheel on the tube 88, so that the tube can be raised and lowered. At the upper end region of the tube 88, the head assembly is mounted. It is electrically connected with the controls in the cabinet 10 by cables passing through the tube 88 and the column 84. There is also a counterweight mechanism (not shown) so that the tube 88 and head assembly can be adjusted easily to any position, and will stay there.

The head assembly includes a head 32, having a cylindrical wall portion 30' and a shell 33 (with vanes 34) spaced from it. A rather short tubular body 30 extends upwardly from the head 32. It contains not one but several (here five) fans 92 distributed around its periphery. These have the same function as the single fan of the first embodiment. However, since the hot air rises through the holes 35 in the shell 33 and passes up around the body, if the air input to the body was again a grille in its end wall, it would tend to suck in the hot air. Therefore there is an air inlet 94 projecting rearwardly of the back of the body.

Within the head 32, there is a parabolic reflector 46 (of copper, with a gilded reflecting surface 47). This is dimensioned so that its radially outer periphery is spaced by about 4 cm from the wall portion 30' to allow the passage of cooling air from the fans 92.

The source of heat and light is a pair of parallel tubular lights 45 of quartz-halogen type. These extend perpendicularly to the axis, adjacent the focus of the reflector 46. They are each about 10 cm long, rated at 300 watts each, and are about 4 cm apart. They are mounted on a girder 96 which extends across the head 32, being mounted within the wall portion 30', (Smaller apparatus uses a single quartz-halogen bulb at the focus, rated at 55 watts.)

The disc 42, with jewels 48 in apertures 43, is planar, and forms the end wall of the head 32.

There may be temperature sensors located within the head 32, for use in controlling the temperature therein, e.g. by controlling the fans 92. The temperature of the stones 48 is believed to be quite important, best results having been obtained with stone temperatures in the range 78°-110° F. (25°-44° C.). To prevent drastic overheating, there may be thermal cut-outs in the power supply to the lights 45. (Of course, sensors and/or cut-outs can also be used in the first embodiment.)

While the basis of the therapeutic effect of the apparatus is not fully understood, and the invention is not tied to any theory, it is noted that some medical opinion associates migraine attacks with some form of imbalance of certain brain cells. Sundry other illnesses are attributed to malfunctions of cells. The activities of the affected cells are believed to go out of their natural frequencies in some way. It seems possible that the radiation transmitted and emitted by the jewels and the silver rotor may in some sense interact with the malfunctioning cells, and cause them to return to their natural frequencies.

The present invention provides apparatus that can be used safely, even on children, without the risks associated with such conventional radiation treatments as those involving X or gamma rays.

Migraine and rheumatic complaints have been mentioned by way of example, but it is believed that other diseases may also be amenable to treatment.

While the invention has been illustrated above by reference to the preferred embodiments, it will be understood by those skilled in the art that various changes may be made without departing from the spirit and scope of the invention, and it is intended to cover all such changes and modifications by the appended claims.

I claim:

1. Therapeutic apparatus for producing a beam of therapeutic radiation, comprising: a source of at least one of thermal and optical radiation, a shield interposed in a path of radiation from the source, said shield including a plate having a plurality of aperatures defined therein, in which a plurality of jewels are mounted, said jewels being of a plurality of types including at least some emeralds, topazes, garnets, sapphires, rubies, diamonds, peridots and amethysts, whereby radiation from the source is transmissible through the shield via at least some of the jewels.

2. Apparatus according to claim 1 wherein in use the shield is heated so that the jewels are substantially within the range 25°-44° C.

3. Apparatus according to claim 2, wherein the heating is effected by the radiation source.

4. Apparatus according to claim 1 wherein the shield is rotatable.

5. Apparatus according to claim 1 wherein there is a reflector having a gold reflecting surface rearwardly of the source.

6. Apparatus according to claim 1 wherein the plate is of silver or of gilded copper.

7. Apparatus according to claim 1 wherein said source comprises at least one electric lamp, the apparatus further including power supply means for selectively supplying thereto alternating or direct current.

8. Apparatus according to claim 1 wherein the jewels (48) are of a plurality of types differing in radiation absorption characteristics.

9. Apparatus according to claim 1 including means for controlling the temperature of the jewels.

10. (new) Apparatus according to claim 1 wherein the jewels are symmetrically distributed about the shield in terms of their types and sizes.

* * * * *